United States Patent
Weyl et al.

[11] Patent Number: 5,942,092
[45] Date of Patent: Aug. 24, 1999

[54] SENSOR

[75] Inventors: Helmut Weyl, Schwieberdingen; Romuald Fries, Weissach; Frank Pelz, Esslingen, all of Germany

[73] Assignee: Robert Bosch GmbH, Stuttgart, Germany

[21] Appl. No.: 08/930,622

[22] PCT Filed: Oct. 25, 1996

[86] PCT No.: PCT/DE96/02041

§ 371 Date: Oct. 7, 1997

§ 102(e) Date: Oct. 7, 1997

[87] PCT Pub. No.: WO97/30345

PCT Pub. Date: Aug. 21, 1997

[30] Foreign Application Priority Data

Feb. 14, 1996 [DE] Germany .......................... 196 05 290

[51] Int. Cl.$^6$ .................................................. G01N 27/407
[52] U.S. Cl. .................. 204/424; 204/426; 204/428; 277/619; 277/630; 277/650; 277/943
[58] Field of Search ................ 204/421–429; 205/783.5, 784, 784.5, 785; 277/619, 630, 650, 943

[56] References Cited

U.S. PATENT DOCUMENTS

| 2,271,936 | 2/1942 | Carson | 277/619 |
|---|---|---|---|
| 2,985,291 | 5/1961 | Schoepe et al. | 277/650 |
| 3,095,619 | 7/1963 | Peterson | 277/650 |
| 3,767,215 | 10/1973 | Brown | 277/650 |
| 4,732,663 | 3/1988 | Kato et al. | 204/427 |
| 5,107,071 | 4/1992 | Nakagawa | 277/650 |
| 5,711,863 | 1/1998 | Henkelmann et al. | 204/427 |

FOREIGN PATENT DOCUMENTS

| 0 087 626 | 9/1983 | European Pat. Off. . |
|---|---|---|
| 0 398 579 | 11/1990 | European Pat. Off. . |
| 43 18 789 | 12/1994 | Germany . |
| WO 92 08127 | 5/1992 | WIPO . |

Primary Examiner—T. Tung
Attorney, Agent, or Firm—Venable; Norman N. Kunitz

[57] ABSTRACT

A sensor device, particularly for determining the oxygen content in exhaust gases of internal combustion engines, having a sensor element that is surrounded gas-tight by a seal and fixed in a housing. The seal (19) is inserted as a pre-sintered, deformable sealing body (19') into the housing (12), between a ceramic molded body on the side of the measured gas and a ceramic molded body on the connection side (18, 20); the pre-sintered sealing body (19') can be deformed under pressure. The ceramic molded parts (18, 20) and the sealing body (19') have respective axially-extending throughgoing holes (32, 42, 52). The sealing body (19') has formed-on structures that narrow the cross section of the throughgoing hole (42) and are deformed by the sensor element (22) when the sensor element (22) is inserted such that the sensor element (22) is stopped, arrested or fixed in the installed position in the throughgoing hole (42) by the formed-on structures. The facing end faces of the ceramic molded parts (18, 20) and of the sealing body (19') each have form-fitting engaging elements that engage one another and rest against the opposite, touching end faces, which engaging elements orient the ceramic molded parts (18, 20) and the sealing body (19') radially such that the respective throughgoing holes (32, 42, 52) extend in alignment with one another.

8 Claims, 2 Drawing Sheets

SENSOR

The invention relates to a sensor device, particularly for determining the oxygen content in exhaust gases of, internal combustion engines, of the type having a sensor element that is surrounded gas-tight by a seal and fixed in a housing, with the seal being inserted into the housing as a deformable sealing body that has an axially-extending throughgoing hole for receiving the sensor element.

DE-OS 41 26 378 discloses a sensor device in which a planar sensor element is fixed in a longitudinal housing bore by means of a seal, with the seal being disposed between two ceramic molded parts. The ceramic molded parts comprise $Al_2O_3$. The seal is a pre-sintered steatite molded body that is deformed through the exertion of a pressure on one of the two ceramic molded parts during installation of the sensor device, and rests in a gas-tight manner against the circumference of the sensor element.

A problem that occurs when the sensor element is installed into the housing of the sensor device is that the sensor element cannot be stopped in the oblong holes of the ceramic molded parts and the sealing body, and can be damaged or destroyed by the hard edges of the ceramic molded bodies due to opposing twisting of the ceramic molded bodies or the sealing body with respect to the ceramic molded parts when the sealing body is pressed.

It is the object of the inventions to simplify the installation of the sensor element, specifically the insertion into the housing, and to increase production reliability and quality.

SUMMARY AND ADVANTAGES OF THE INVENTION

The above object generally is achieved according to a first feature of the invention by a sensor device, particularly for determining the oxygen content in exhaust gases of internal combustion engines, having a sensor element that is surrounded gas-tight by a seal and fixed in a housing, wherein: the seal is inserted into the housing as a deformable sealing body that has an axially-extending throughgoing hole for receiving the sensor element; the sealing body has formed-on structures that narrow the cross section of the throughgoing hole and are permanently deformed when the sensor element is inserted such that the sensor element is stopped and secured in the throughgoing hole by at least the formed-on structures.

The above object generally likewise is achieved according to a further feature of the invention by a sensor device, particularly for determining the oxygen content in exhaust gases of internal combustion engines, having a sensor element that is surrounded gas-tight by a seal and fixed in a housing, wherein: the seal is inserted into the housing as a deformable sealing body that is disposed between at least one ceramic molded part on the side of the measured gas and at least one connection-side ceramic molded part; the sealing body and the ceramic molded parts respectively have an axially-extending throughgoing hole for receiving the sensor element: the ceramic molded part on the side of the measured gas, the connection-side ceramic molded part and the sealing body each have form-fitting engaging elements that engage one another and rest against the adjacent opposite, touching end faces; and the form-fitting engaging elements are oriented radially with respect to the respective throughgoing holes such that the throughgoing holes extend in alignment with one another.

The sensor devices according to the invention, as described above, the have the advantage that the installation step of inserting the sensor element into the housing is simplified and, at the same time, the production reliability and quality of the sensor are improved. The invention according to the feature above effects the stopping arresting or fixing of the sensor element in the sealing body, so the sensor element retains its axial installed position upon insertion into the housing. With the invention according to the second feature, the throughgoing holes of the ceramic molded parts and the sealing body, which are configured as oblong holes in cross-section, are compelled to experience a radial orientation during installation, so the edges of the ceramic molded parts cannot damage or break the sensor element during pressing. The combination of the inventions according to both features results in a particularly high production reliability and facilitation of installation.

Advantageous modifications of and improvements to the sensor device disclosed in the main claims are possible with the measures disclosed in the dependent claims. This relates in particular to the embodiment of formed-on deformable structures that narrow the cross section of the oblong holes such that the sensor element is stopped or arrested gently as well as relatively securely in the sealing body. It is also especially advantageous to configure the form-fitting means for radial orientation at a right angle to the long side of the oblong holes.

BRIEF DESCRIPTION OF THE DRAWINGS

Two embodiments of the invention are illustrated in the drawings and described in detail in the following description.

EMBODIMENTS

Figure 1:
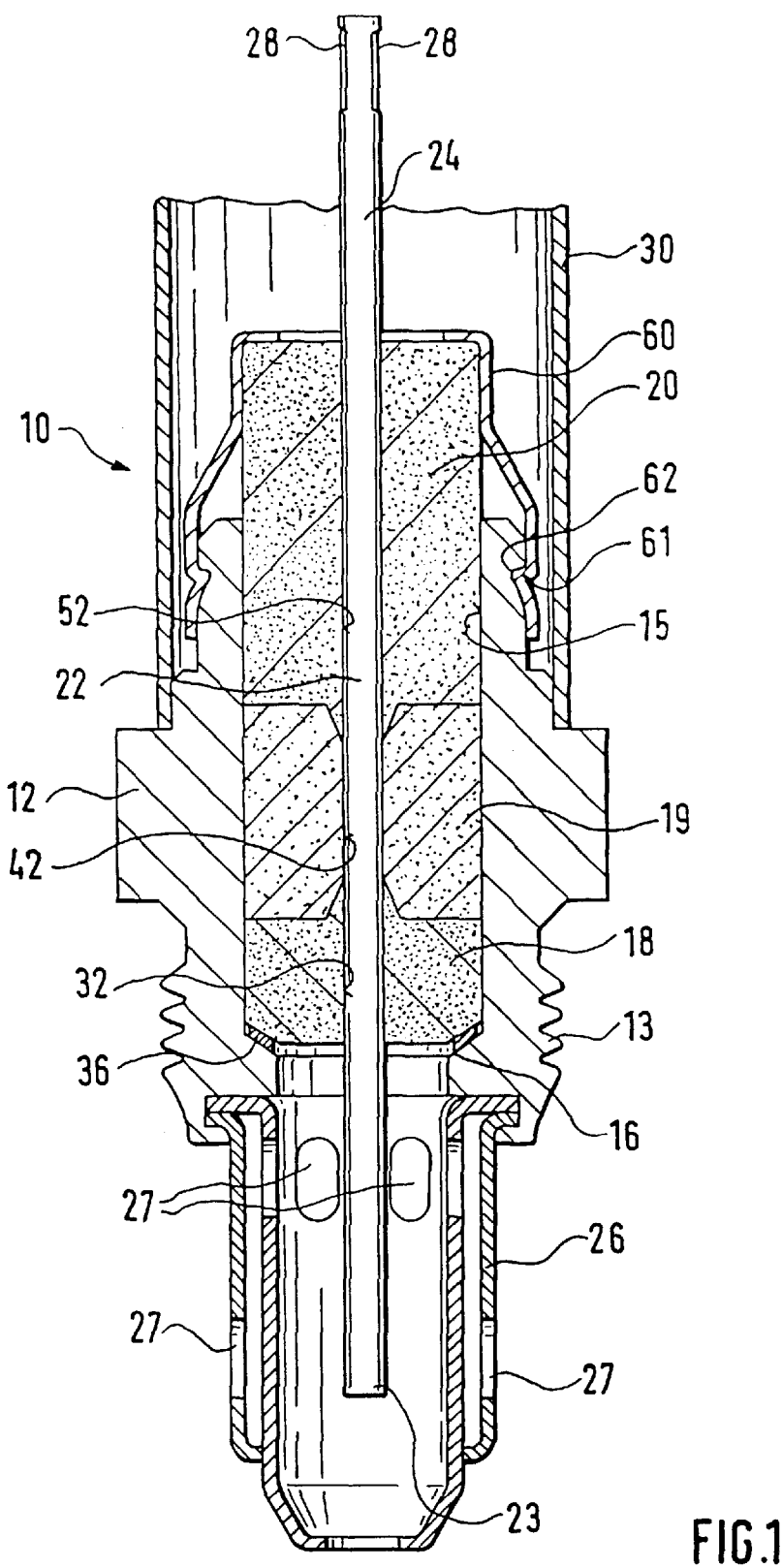
FIG. 1 shows a cross-section of a part of a sensor device on the side of the measured gas.

FIG. 1 shows a section of a gas sensor 10, for example an electrochemical oxygen sensor, on the side of the measured gas. The sensor has a metal housing 12 that is provided with a thread 13 as a securing means for installation into a measured-gas pipe, not shown. The housing 12 has a longitudinal bore 15 with a shoulder-shaped annular surface 16. A ceramic molded part 18 on the side of the measured gas, as well as a seal 19 and a ceramic molded part 20 on the connection side, are disposed in the longitudinal bore 15. A planar sensor element 22 that has a section 23 on the side of the measured gas and a section 24 on the connection side extends through the ceramic molded parts 18, 20 and the seal 19.

Figure 3A:
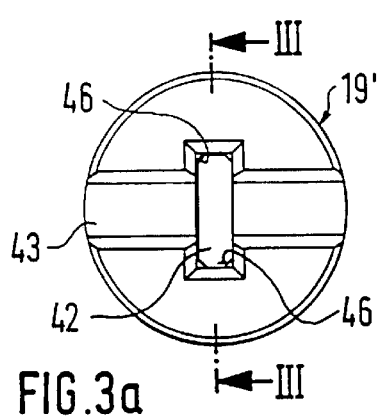
FIG. 3b shows a section through the sealing body of FIG. 3a along line III—III.
FIG. 3c is a front view of a sealing body in a second embodiment.
Figure 3B:
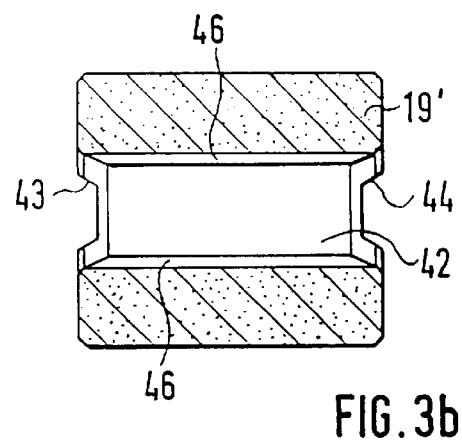
Figure 3C:
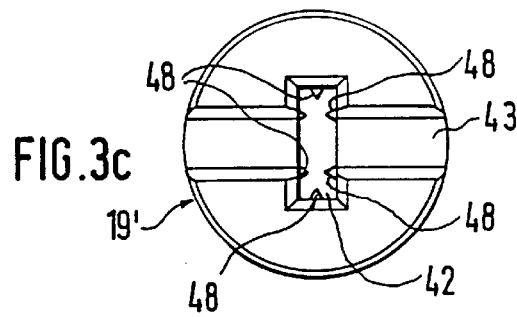

The ceramic molded parts 18 and 20 comprise an electrically-insulating ceramic, for example $Al_2O_3$. The seal 19 comprises steatite or boron nitride. Prior to installation into the longitudinal bore 15 of the housing 12, the seal 19 obtains the form of a preform that is created through pressing of steatite powder or boron nitride powder to form a sealing body 19' (FIGS. 3a, 3b, 3c). The ceramic molded parts 18, 20 are significantly harder than the sealing body 19', and cannot be deformed.

The section 23 of the sensor element 22 on the side of the measured gas projects out of the housing 12, and is surrounded by a protective pipe 26 secured to the housing 12. The protective pipe 26 has entrance and exit openings 27 for the gas to be measured.

The section 24 on the connection side has connection contacts 28, which likewise project out of the housing 12. The connection contacts 28 are contacted with a contact plug provided with connecting cables. The section 24 projecting out of the housing 12 on the side of the measured gas is surrounded by a metal sleeve 30 that is welded gas-tight to the housing 12. The sleeve 30 protects the connection-side section 24 from environmental influences, and has an opening, not shown, through which the connecting cables are guided to the outside. The opening is closed in a manner known per se by a cable bushing.

Figure 2A:
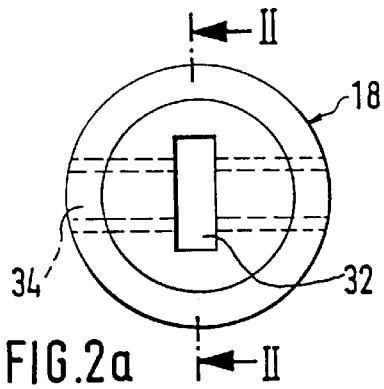
FIG. 2a is a front view of a ceramic molded part on the side of the measured gas.
Figure 2B:
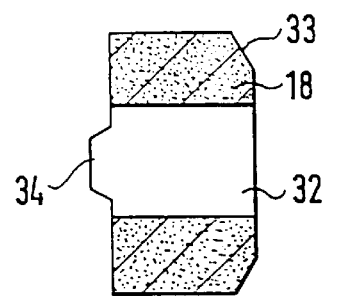
FIG. 2b shows a section through the ceramic molded part of FIG. 2a along line II—II; 3a is a front view of a sealing body in a first embodiment.

In FIGS. 2a and 2b, the ceramic molded part 18 on the side of the measured gas is cylindrical and has an axial-symmetrically-extending throughgoing hole 32, which has, for example, a rectangular cross section suitable for guiding the planar sensor element 22 through. The end face of the ceramic molded part 18 on the side of the measured gas is provided with a slant 33, and the opposite end face is provided with a projection 34 that protrudes, for example, in trapezoidal form from the associated end face. The projection 34 extends over the entire diameter of the cylindrical ceramic molded body, at a right angle with respect to the long side of the rectangular throughgoing hole 32. The slant 33 of the ceramic molded part 18 is seated on a metal sealing ring 36 positioned on the annular surface 16 of the housing 12.

FIGS. 3a, 3b and 3c show the sealing body 19' prior to installation into the longitudinal bore 15 of the housing 12. The sealing body 19' also has an axial-symmetrically-extending throughgoing hole 42 that has a rectangular cross section. The sealing body 19' further has a first cutout 43 at one end face, and a second cutout 44 at the other end face. The cutouts 43, 44 respectively extend over the diameter of the end face or surface of the sealing body 19', and likewise extend at a right angle with respect to the long side of the rectangular throughgoing hole 42.

Fixing means for the sensor element 22 are formed into the rectangular throughgoing hole 42 of the sealing body 19'; at certain locations, these means narrow the cross section of the throughgoing hole 42. In a first embodiment, the fixing means are configured as chamfers 46 formed onto the four inside edges of the rectangular throughgoing hole 42. The dimensions of the rectangular throughgoing hole 42 and the chamfers 46 are selected such that the completely-sintered, planar sensor element 22, which is a hard, brittle ceramic body, can be pressed through the throughgoing hole 42 with a low expenditure of force; the edges of the sensor element 22 deform or scrape the chamfers 46 so the sensor element 22 is stopped, arrested or fixed in the throughgoing hole 42.

A second embodiment of the fixing means ensues from FIG. 3c. Here, tooth-shaped projections 48 are formed onto opposite inside surfaces of the throughgoing hole 32. Like the chamfers 46 of the first embodiment, the tooth-shaped projections 48 are configured such that the sensor element 22 scrapes or deforms the projections 48 under slight pressure during insertion, thus fixing the sensor element 22 in the throughgoing hole 42.

Figure 4A:
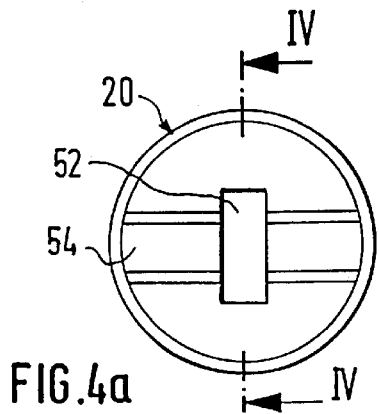
FIG. 4a is a front view of a ceramic molded part on the connection side.
Figure 4B:
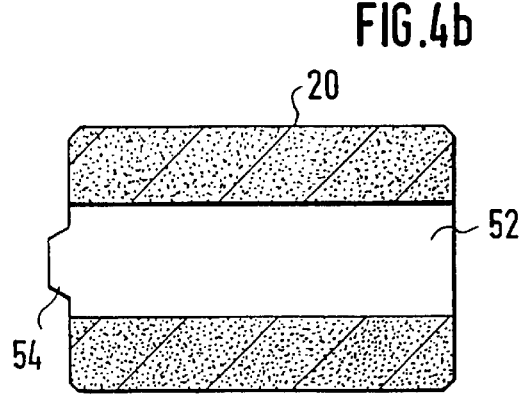
FIG. 4b is a sectional representation through the ceramic molded part in FIG. 4a along line IV—IV.

In FIGS. 4a and 4b, the ceramic molded part 20 on the connection side also has an axial-symmetrically-extending throughgoing hole 52 that has a rectangular cross section. The ceramic molded part 20 further has at one end face a projection 54, configured as, for example, a trapezoid that extends over the diameter of the ceramic molded part at a right angle to the long side of the rectangular throughgoing hole 52.

In the installation of the sensor device 10, first the sealing ring 36 is placed on the annular surface 16 of the housing 12. Afterward, the ceramic molded part 18 on the side of the measured gas is placed onto the sealing ring 36. The sealing body 19' is placed onto the ceramic molded part 18, and the projection 34 that protrudes out of the end face of the ceramic molded part 18 extends into the one cutout 43. The sensor element 22 is pushed through the throughgoing hole 42 with little force. As already described, the chamfers 46 or tooth-shaped projections 48 are deformed, and the sensor element 22 is stopped or fixed in the necessary installed position. Now the ceramic molded part 20 on the connection side is guided via the connection-side end 24 of the sensor element 22, and placed onto the sealing body 19. The projection 54 formed on the ceramic molded part 20 extends into the cutout 44 of the sealing body 19'.

It is, however, also conceivable to connect the sensor element to the sealing body outside of the housing, and then place the sensor element 22, with the sealing body 19, onto the ceramic molded part 18 on the side of the measured gas. It is also possible, on the other hand, to first place the connection-side ceramic molded part 20 onto the inserted sealing body 19'. With the projections 34, 54 and the cutouts 43, 44, the throughgoing holes 32, 42, 52 attain a coinciding radial position, so the sensor element 22 can subsequently be pushed through the throughgoing holes 52, 42 and 32 with little pressure and without difficulty.

After the sensor element 22 has attained its installed position, a pressure sleeve 60 having a plurality of uniformly-distributed, inwardly-pointing claws 61 that engage notches 62 formed into the housing is placed onto the connection-side ceramic molded part 20 projecting from the housing 12.

In the initial state, the sealing body 19' is in the longitudinal bore 15 of the housing 12, between the two ceramic molded parts 18 and 20. A pressing force is now exerted on the connection-side ceramic molded part 20 and transmitted to the sealing body 19'. The amount of pressing force is selected such that the pressed sealing body 19' is crushed, and the powder components press against the longitudinal bore 15 of the housing 12 and the sensor element 22. The deformation of the sealing body 19' thus effects the gas- and gasoline-tight seal 19 in the housing 12.

We claim:

1. Sensor device, particularly for determining the oxygen content in exhaust gases of internal combustion engines, having a sensor element that is to be surrounded gas-tight by a seal and fixed in a housing, and wherein the seal is inserted into the housing as a deformable, precompressed sealing body that has an axially-extending throughgoing hole for receiving the sensor element, the sealing body consists of a compressible powder and has inwardly directed non-continuous formed-on structures that narrow the cross section of the throughgoing hole and were partially permanently deformed when the sensor element was inserted such that the sensor element is fixed, at least in the throughgoing hole, by at least the partially deformed formed-on structures.

2. Sensor device according to claim 1, wherein the throughgoing hole has a rectangular cross section and the formed-on structures that narrow the cross section are chamfers formed onto the edges of the throughgoing hole.

3. Sensor device according to claim 1, wherein the throughgoing hole has a rectangular cross section; and the formed-on structures that narrow the cross section are configured as oppositely-located, tooth-shaped projections.

4. Sensor device according to claim 1, wherein the formed-on structures are not as hard as the sensor element.

5. Sensor device, particularly for determining the oxygen content in exhaust gases of internal combustion engines, having a sensor element that is to be surrounded gas-tight by a seal and fixed in a housing; and wherein: the seal is inserted into the housing as a deformable precompressed sealing body formed of a compressible powder that is disposed between at least one ceramic molded part on the side of the measured gas and at least one connection-side ceramic molded part such that the respective end faces of the sealing body are opposite and touch respective facing end faces of the respective ceramic molded parts; the sealing body and the ceramic molded parts each have a respective axially-extending throughgoing hole receiving the sensor element; the facing end faces of the ceramic molded part on the side of the measured gas, the connection-side ceramic molded part and the sealing body each have respective form-fitting engaging elements that engage one another and rest against the opposite, touching end faces; and the form-fitting engaging elements are oriented radially with respect to the respective throughgoing holes such that the throughgoing holes extend in alignment with one another.

6. Sensor device according to claim 5, wherein each of the throughgoing holes have a rectangular cross section, and the form-fitting engaging elements are each disposed at a right angle to the long side of the respective rectangular throughgoing holes and symmetrically with respect to a plane extending through the center point of the cross section.

7. Sensor device according to claim 5, wherein: at the ceramic molded part on the side of the measured gas and at the connection-side ceramic molded part, the respective form-fitting engaging elements are configured as projections that protrude beyond the respective end face, and corresponding cutouts are provided at the respective end faces of the sealing body, which cutouts are engaged by the respective projection.

8. Sensor device, particularly for determining the oxygen content in exhaust gases of internal combustion engines, having a sensor element that is to be surrounded gas-tight by a seal and fixed in a housing, and wherein: the seal is inserted as a pre-sintered, deformable sealing body, consisting of a compressible powder, into the housing, and is disposed between a ceramic molded part on the side of the measured gas and a further ceramic molded part on the connection side such that the respective ends faces of the sealing body are opposite and touch respective facing end faces of the respective ceramic molded parts; the sealing body and the ceramic molded parts each have a respective axially-extending throughgoing hole receiving the sensor element; the sealing body has formed-on structures that narrow the cross section of the throughgoing hole and were partially deformed when the sensor element was inserted such that the sensor element is fixed in the throughgoing hole of the sealing body by the deformed formed-on structures; the facing end faces of the ceramic molded part on the side of the measured gas, the connection-side ceramic molded part and the sealing body each have respective form-fitting engaging elements that engage one another and rest against the opposite, touching end faces; and, the form-fitting engaging elements are oriented radially with respect to the respective throughgoing holes such that the throughgoing holes extend in alignment with one another.

\* \* \* \* \*